United States Patent [19]

Trust et al.

[11] 4,159,375

[45] Jun. 26, 1979

[54] 6- AND 7-ARYL-1,2,4-TRIAZOLO[4,3,b]-1,2,4-TRIAZINES

[75] Inventors: Ronald I. Trust, Monsey; Jay D. Albright, Nanuet, both of N.Y.

[73] Assignee: American Cyanamid Company, Stamford, Conn.

[21] Appl. No.: 936,442

[22] Filed: Aug. 24, 1978

[51] Int. Cl.$^2$ .................... A61K 31/41; C07D 487/04
[52] U.S. Cl. .................................. 544/184; 424/250
[58] Field of Search ........................................ 544/184

[56] References Cited

U.S. PATENT DOCUMENTS

| | | | |
|---|---|---|---|
| 3,333,961 | 8/1967 | Fry et al. ............................. | 544/184 |
| 3,813,393 | 5/1974 | Andrews et al. ..................... | 544/184 |

FOREIGN PATENT DOCUMENTS

| | | | |
|---|---|---|---|
| 1026321 | 3/1958 | Fed. Rep. of Germany ........... | 544/184 |
| 1042471 | 9/1966 | United Kingdom ..................... | 544/184 |

OTHER PUBLICATIONS

Fusco et al., "Chemical Abstracts," vol. 50, 1956, Cols. 10742(h)–10743(a).
Dornow et al., "Chemical Abstracts," vol. 61, 1964, Cols. 11999(d)–12002(g).
Taylor, Jr. et al., "Jour. Amer. Chem. Soc.," vol. 76, 1954, pp. 619–620.

*Primary Examiner*—Donald G. Daus
*Assistant Examiner*—James H. Turnipseed
*Attorney, Agent, or Firm*—Edward A. Conroy, Jr.

[57] ABSTRACT

This application discloses 6- or 7-(o-, m- or p-substituted-phenyl)-1,2,4-triazolo[4,3-b]-1,2,4-triazines useful as anxiolytic agents.

8 Claims, No Drawings

6- AND 7-ARYL-1,2,4-TRIAZOLO[4,3-B]-1,2,4-TRIAZINES

BRIEF SUMMARY OF THE INVENTION

This invention relates to new organic compounds and, more particularly, is concerned with novel 6- or 7-(ortho-, meta- or para-substituted-phenyl)-1,2,4-triazolo[4,3-b]-1,2,4-triazines which may be represented by the following structural formula:

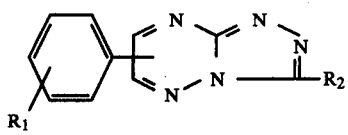

wherein $R_1$ is halogen, trifluoromethyl or lower alkoxy and $R_2$ is hydrogen or lower alkyl. Suitable lower alkyl and lower alkoxy groups contemplated by the present invention are those having from one to four carbon atoms such as methyl, ethyl, isopropyl, sec-butyl, methoxy, ethoxy, n-propoxy, isobutoxy, etc. whereas halogen is exemplified by fluoro, chloro and bromo. The novel compounds of the above general formula are yellow to orange crystalline solids which are generally soluble in lower alkanols, acetone, toluene and chlorinated solvents such as chloroform, dichloromethane, and the like but are sparingly soluble in water.

DETAILED DESCRIPTION OF THE INVENTION

The novel 7-(o-, m- or p-substituted-phenyl)-1,2,4-triazolo[4,3-b]-1,2,4-triazines (V) of the present invention may be readily prepared as set forth in the following reaction scheme:

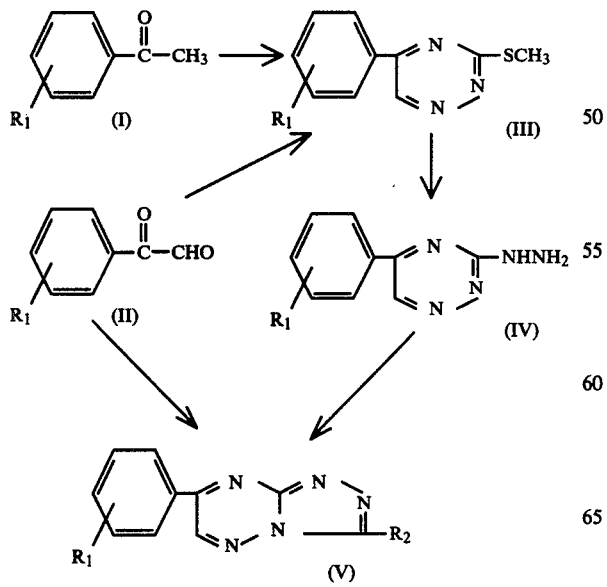

wherein $R_1$ and $R_2$ are as hereinbefore defined. In accordance with the above reaction sequence, an appropriate ortho-, meta- or para-substituted acetophenone (I) is refluxed overnight in a mixture of selenium dioxide, dioxane, and water. The precipitated selenium is removed by filtration and to the filtrate is added ice, sodium bicarbonate, and 3-methyl-isothiosemicarbazide hydroiodide. Stirring of this mixture for several hours at room temperature then provides the corresponding 5-(o-, m- or p-substituted-phenyl)-3-methylthio-1,2,4-triazine (III). Alternatively, an appropriate ortho-, meta- or para-substituted phenylglyoxal (II) and 3-methyl-isothiosemicarbazide in 50% aqueous ethanol is stirred overnight at $-10°$ to $+10°$ C. in the presence of sodium carbonate to provide the corresponding 3-methylthio-1,2,4-triazine (III) directly. Treatment of the 3-methylthio-1,2,4-triazine (III) with 95% hydrazine hydrate in 50% methanol-tetrahydrofuran at the reflux temperature for 12-24 hours provides the corresponding 5-(o-, m- or p-substitutedphenyl)-3-hydrazine-1,2,4-triazine (IV). Cyclization of (IV) to the 7-substituted-phenyl-1,2,4-triazolo[4,3-b]-1,2,4-triazines (V) is accomplished by refluxing for 2-4 hours with excess of an ortho ester of the formula $R_2$—$C(OR)_3$ wherein R is methyl or ethyl and $R_2$ is as hereinabove defined. Alternatively, an appropriate phenylglyoxal (II) may be condensed with a 3,4-diamino-4H-1,2,4-triazole of the formula:

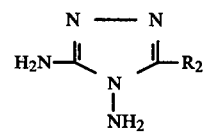

wherein $R_2$ is as hereinabove defined to provide the corresponding final product (V). This condensation is best carried out in 67% acetic acid in the presence of sodium acetate at 90°-100° C. for ½-2 hours.

The novel 6-(o-, m- or p-substituted-phenyl)-1,2,4-triazolo[4,3-b]-1,2,4-triazines (XI) of the present invention may be readily prepared as set forth in the following reaction scheme:

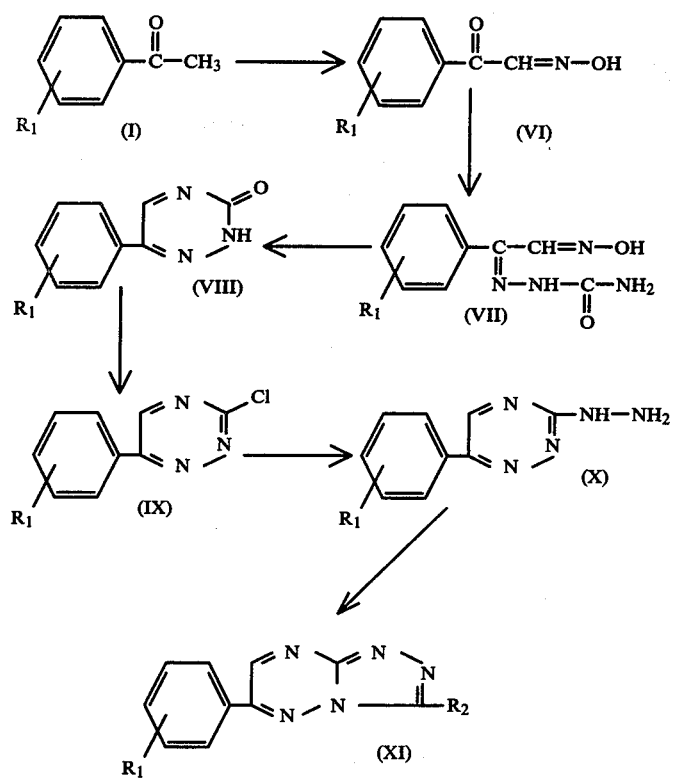

wherein $R_1$ and $R_2$ are as hereinbefore defined. In accordance with the above reaction sequence, an appropriate ortho-, meta- or para-substituted acetonphenone (I) is refluxed overnight in a mixture of selenium dioxide, dioxane, and water. The precipitated selenium is removed by filtration and the filtrate is diluted with water, adjusted to pH 4, and mixed with acetone oxime producing the corresponding phenylglyoxaldoximes (VI) after stirring at room temperature for 3–4 days. Treatment of (VI) with semicarbazide hydrochloride and sodium acetate in 50% aqueous ethanol at 50°–60° C. for 2–4 hours provides the corresponding phenylglyoxaldoxime semicarbazones (VII). Cyclization of (VII) to the 6-substituted-phenyl-1,2,4-triazin-3(2H)-ones (VIII) is accomplished by first refluxing in 5% hydrochloric acid for one hour, and then refluxing the so-produced solid in glacial acetic acid overnight. Treatment of (VIII) with phosphorus oxychloride in chloroform in the presence of N,N-dimethylformamide at the reflux temperature for 3–6 hours provides the corresponding 6-substituted-phenyl-3-chloro-1,2,4-triazines (IX). The conversion of (IX) to the corresponding 3-hydrazine derivatives (X) is achieved by treatment with hydrazine hydrate in pyridine as solvent for one hour at room temperature. Cyclization of (X) to the 6-substituted-phenyl-1,2,4-triazolo[4,3-b]-1,2,4-triazines (XI) is accomplished by refluxing for 2–4 hours with excess of an ortho ester of the formula $R_2$—C(OR)$_3$ wherein R is methyl or ethyl and $R_2$ is as hereinabove defined.

The novel compounds of the present invention possess central nervous system activity at non-toxic doses and as such are useful as anxiolytic agents. That is, they produce certain responses in standard tests with laboratory animals which are known to correlate well with relief of anxiety in man. When tested pharmacologically, the compounds of this invention have such properties with a desirable wide spread between doses producing anxiolytic activity and toxic symptoms.

The anti-anxiety properties of the compounds of this invention have been established in a test which indicates anxiolytic activity by the measure of protection from convulsions resulting from the administration of pentylenetetrazole. Single or graded dose levels of the test compounds were administered orally or intraperitoneally in a 2% starch vehicle, to groups of at least 4 rats. At 30 or 60 minutes, the rats were treated intravenously with pentylenetetrazole at a dose of 21 to 23 mg./kg. of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp. 237–288 (1971)] that there is a high degree of correlation between antagonism of pentylenetetrazole seizures in rats and anti-anxiety effects in higher warm-blooded animals. Representative compounds of the present invention were considered active when tested by this procedure.

Another test which has been used to asses anti-anxiety effect is a non-conditioned passive avoidance procedure described by J. R. Vogel, B. Beer and D. E. Clody, "A Simple and Reliable Conflict Procedure for Testing Anti-Anxiety Agents", Psychopharmacologia, 21, 1–7 (1971). A conflict situation is induced in rats by a modification of this method.

Groups of 6 naive, Wistar strain rats, weighing 200–240 g. each are deprived of water for 48 hours and food for 24 hours. The test compounds were administered in single or graded, oral or intraperitoneal doses, suspended in a 2% starch vehicle containing 0.5% v/v polyethylene glycol and one drop of polysorbate 80. Control animals receive the vehicle alone. At 30 or 60 minutes each rat is placed in an individual black plexiglass chamber. A 10% dextrose solution is available ad libitum from a tap located in the rear of the chamber. A 0.3 milliampere constant current 60 Hz pulsed DC shocking current is established between the stainless steel grid floor and the tap. After 20 seconds of non-shocked drinking, an alternating 5 second "shock-on" and 5 second "shock-off" cycle begins and is continued for a total of 5 minutes. The number of shocks taken by each rat during the 5 minute interval is recorded and compared to a control group. The test compounds are considered active if the shocks received by the test group are significantly different from the control group by the Mann-Whitney U test. Representative compounds of this invention were considered active when tested by this procedure.

The novel compounds of the present invention have been found to be highly useful for meliorating anxiety in mammals when administered in amounts ranging from about 0.05 mg. to about 15.0 mg./kg. of body weight per day. A preferred dosage regimen for optimum results would be from about 0.5 mg. to about 10.0 mg./kg. of body weight per day. Such dosage units are employed that a total of from about 35.0 mg. to about 700 mg. of active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compounds may be administered in any convenient manner such as by the oral, intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 0.1 and 5.0 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

This invention will be described in greater detail in conjunction with the following specific examples. The following examples are given for the purpose of illustration and are not intended to limit the scope of the invention.

EXAMPLE 1

7-(p-Chlorophenyl)-1,2,4-triazolo[4,3-b]-1,2,4-triazine

To a slurry of 25.5 g. of p-chlorophenylglyoxal and 43.7 g. of 3-methyl iso-thiosemicarbazide hydroiodide in 500 ml. of 50% ethanol, maintained at 0° C., is added 18.5 g. of sodium bicarbonate. The mixture is stirred overnight. The solid is collected by filtration and recrystallized, with charcoal treatment, from ethanol giving 11.3 g. of 5-(p-chlorophenyl)-3-(methylthio)-1,2,4-triazine as yellow needles.

To a solution of 10.66 g. of 5-(p-chlorophenyl)-3-(methylthio)-1,2,4-triazine in 60 ml. of 1:1 methanol-tetrahydrofuran is added 2.42 g. of 95% hydrazine. The mixture is refluxed overnight, cooled and the solid is recovered by filtration, giving 8 g. of 5-(p-chlorophenyl)-3-hydrazino-1,2,4-triazine as orange plates.

A mixture of 4.4 g. of 5-(p-chlorophenyl)-3-hydrazino-1,2,4-triazine and 20 ml. of ethyl orthoformate is refluxed for 4 hours cooled and filtered giving the desired product as light yellow plates, m.p. >300° C.

EXAMPLE 2

7-(p-Chlorophenyl)-3-methyl-1,2,4-triazolo[4,3-b]-1,2,4-triazine

A solution of 7.8 g. of p-chlorophenylglyoxal, 6.3 g. of 3,4-diamino-5-methyl-4H-1,2,4-triazole hydrochloride and 1.7 g. of sodium hydroxide in 90 ml. of 67% acetic acid is heated on a steam bath for ½ hour. Water is added and heating is continued until yellow crystals separate. These crystals are collected by filtration and washed with hot ethanol, giving the desired product as a yellow solid, m.p. 240° C. (dec.).

EXAMPLE 3

7-(p-Methoxyphenyl)-1,2,4-triazolo[4,3-b]-1,2,4-triazine

A solution of 9.1 g. of p-methoxyphenylglyoxal, 6.7 g. of 3,4-diamino-4H-1,2,4-triazole and 4.1 g. of sodium acetate in 90 ml. of 67% acetic acid is heated on a steam bath for ½ hour. Water is added and heating is continued until crystals separate. The mixture is cooled and filtered. The precipitate is washed with water, ethanol and then hexane giving the desired product as yellow plates, m.p. 282.5°–284.5° C.

EXAMPLE 4

7-(p-Fluorophenyl)-1,2,4-triazolo[4,3-b]-1,2,4-triazine

A solution of 11.9 g. of p-fluorophenylglyoxal, 9.5 g. of 3,4-diamino-4H-1,2,4-triazole and 5.74 g. of sodium acetate in 120 ml. of 67% acetic acid is heated on a steam bath and then filtered through celite. The filtrate is heated for an additional hour and the resulting solid is collected by filtration giving the desired product as cream-colored plates, m.p. >300° C.

EXAMPLE 5

7-(α,α,α-Trifluoro-m-tolyl)-1,2,4-triazolo[4,3-b]-1,2,4-triazine

A solution of 12.5 g. of m-trifluoromethylphenylglyoxal, 7.69 g. of 3,4-diamino-4H-1,2,4-triazole and 4.67 g. of sodium acetate in 120 ml. of 67% acetic acid is reacted as described in Example 4, giving the desired product as a yellow solid, m.p. 288°–290° C. (dec.).

EXAMPLE 6

7-(o-Chlorophenyl)-1,2,4-triazolo[4,3-b]-1,2,4-triazine

A solution of 14 g. of o-chlorophenylglyoxal, 10.6 g. of 3,4-diamino-4H-1,2,4-triazole and 6.3 g. of sodium acetate in 180 ml. of 67% acetic acid is heated on a steam bath and then filtered through celite. The filtrate is heated for an additional hour and then allowed to stand at room temperature for several days, producing the desired product as a cream colored solid, m.p. 162°–165° C.

EXAMPLE 7

7-(p-Fluorophenyl)-3-methyl-1,2,4-triazolo[4,3-b]-1,2,4-triazine

A 17 g. portion of p-fluorophenylglyoxal is heated in 50% ethanol on a steam bath and then filtered through celite. Water is added to the filtrate and the mixture is cooled. A 12.6 g. portion of sodium bicarbonate is added forming an orange suspension. A 32.6 g. portion of 3-methyl-isothiosemicarbazide hydroiodide in a mixture of 300 ml. of ice and water is added producing a solid which is collected by filtration and washed with water, methanol and hexane giving 5-(p-fluorophenyl)-3-(methylthio)-1,2,4-triazine as a solid.

To a solution of 11.9 g. of 5-(p-fluorophenyl)-3-(methylthio)-1,2,4-triazine in 50 ml. of 1:1 methanol-tetrahydrofuran is added 2.1 ml. of 95% hydrazine. The mixture is refluxed for 12 hours and then cooled. The solid which forms is collected by filtration and washed with hexane, giving 5-(p-fluorophenyl)-3-hydrazino-1,2,4-triazine as a yellow solid.

A mixture of 0.57 g. of 5-(p-fluorophenyl)-3-hydrazino-1,2,4-triazine and 20 ml. of ethyl orthoacetate is refluxed for 4 hours, cooled and filtered. The desired product is recovered as a brown solid, m.p. 227.5°–231° C.

EXAMPLE 8

7-(o-Fluorophenyl)-1,2,4-triazolo[4,3-b]-1,2,4-triazine

To a solution of 22.2 g. of selenium dioxide in 150 ml. of dioxane and 4.5 ml. of water at 55° C. is added 27.6 g. of o-fluoroacetophenone. The mixture is refluxed overnight, cooled and the precipitated selenium is removed by filtration. To the filtrate is added 200 g. of ice and 25.2 g. of sodium bicarbonate followed by a saturated solution of 58.25 g. of 3-methyl isothiosemicarbazide hydroiodide. The mixture is stirred for several hours and then the solid which forms is collected by filtration. Recrystallization from ethanol gives 5-(o-fluorophenyl)-3-(methylthio)-1,2,4-triazine as a yellow solid.

To a solution of 27.6 g. of 5-(o-fluorophenyl)-3-(methylthio)-1,2,4-triazine in 100 ml. of 1:1 methanol-tetrahydrofuran is added 6.4 ml. of 95% hydrazine. The mixture is refluxed for about 22 hours and then cooled. The solid is recovered by filtration, giving 5-(o-fluorophenyl)-3-hydrazino-1,2,4-triazine as yellow crystals.

A mixture of 1.85 g. of 5-(o-fluorophenyl)-3-hydrazino-1,2,4-triazine and 20 ml. of ethyl orthoformate is refluxed for 4 hours, cooled and the solid is collected and washed with hexane giving the desired product as yellow crystals, m.p. 171°–173.5° C.

EXAMPLE 9

6-(o-Chlorophenyl)-3-methyl-1,2,4-triazolo[4,3-b]-1,2,4-triazine

A 31.2 g. portion of o-chloroacetophenone is converted to 5-(o-chlorophenyl)-3-(methylthio)-1,2,4-triazine essentially by the method described in Example 8.

A 29.6 g. portion of 5-(o-chlorophenyl)-3-(methylthio)-1,2,4-triazine is converted to 5-(o-chlorophenyl)-3-hydrazino-1,2,4-triazine essentially by the method described in Example 8.

A mixture of 6.65 g. of 5-(o-chlorophenyl)-3-hydrazino-1,2,4-triazine and 50 ml. of ethyl orthoacetate is refluxed for 2.5 hours, cooled and the solid collected by filtration and washed with hexane and ethanol, giving the desired product as yellow crystals, m.p. 192°–196.5° C.

EXAMPLE 10

7-(o-Fluorophenyl)-3-methyl-1,2,4-triazolo[4,3-b]-1,2,4-triazine

A mixture of 6.15 g. of 5-(o-fluorophenyl)-3-hydrazino-1,2,4-triazine and 50 ml. of ethyl orthoacetate is refluxed for 2.5 hours, cooled and the solid is collected by filtration and washed with hexane and ethanol, giving the desired product as yellow crystals, m.p. 227°–229° C.

EXAMPLE 11

3-Methyl-7-(α,α,α-trifluoro-m-tolyl)-1,2,4-triazolo[4,3-b]-1,2,4-triazine

A 37.6 g. portion of m-trifluoromethylacetophenone is converted to 3-methylthio-5-(α,α,α-trifluoro-m-tolyl)-1,2,4-triazine essentially by the method described in Example 8.

To a solution of 22.8 g. of 3-methylthio-5-(α,α,α-trifluoro-m-tolyl)-1,2,4-triazine in a mixture of 30 ml. of methanol and 35 ml. of tetrahydrofuran is added 4.84 ml. of 95% hydrazine. The mixture is refluxed for 48 hours, cooled and the solid is collected by filtration giving 3-hydrazino-5-(α,α,α-trifluoro-m-tolyl)-1,2,4-triazine as yellow needles.

A mixture of 5.1 g. of 3-hydrazino-5-(α,α,α-trifluoro-m-tolyl)-1,2,4-triazine and 60 ml. of ethyl orthoacetate is refluxed for 2.5 hours, cooled and the solid is collected by filtration and washed with hexane and ethanol, giving the desired product as yellow plates, m.p. 230°–233° C.

EXAMPLE 12

6-(p-Fluorophenyl)-1,2,4-triazolo[4,3-b]-1,2,4-triazine

To a solution of 29.5 g. of selenium dioxide in 200 ml. of dioxane and 6 ml. of water at 55° C. is added 50 g. of p-fluoroacetophenone. The mixture is refluxed overnight and the precipitated selenium is removed by filtration. The filtrate is added to an equal volume of water and adjusted to pH 4 with 5% aqueous sodium hydroxide. To this solution is added 20.5 g. of acetone oxime and the mixture is stirred at room temperature for 4 days. Dilution with 2 liters of water and chilling produces a solid which is collected and recrystallized from 50% ethanol, giving p-fluorophenylglyoxaldoxime.

A solution of 71.5 g. of p-fluorophenylglyoxaldoxime, 47.7 g. of semicarbazide hydrochloride and 58.4 g. of sodium acetate trihydrate in 1500 ml. of 50% ethanol is heated to 50°–60° C. for 3 hours producing a solid which is collected and recrystallized from one liter of 50% ethanol giving p-fluorophenylglyoxaldoxime semicarbazone.

A mixture of 61 g. of p-fluorophenylglyoxaldoxime semicarbazone in 1700 ml. of 5% hydrochloric acid is refluxed for one hour, cooled and the solid is collected by filtration, washed with water and dried. This solid is refluxed in 400 ml. of acetic acid overnight. The solvent is removed in vacuo and the residue is scratched with ethanol-hexane giving as a solid 6-(p-fluorophenyl)-1,2,4-triazin-3(2H)-one.

A suspension of 20 g. of 6-(p-fluorophenyl)-1,2,4-triazin-3(2H)-one in 158 ml. of chloroform is cooled in an ice bath and 178.5 ml. of phosphorus oxychloride is added followed by 1.2 g. of N,N-dimethylformamide. The mixture is refluxed for 4.5 hours and then the excess phosphorus oxychloride is removed in vacuo. The residue is redissolved in chloroform and poured into icewater. When the ice melts the mixture is filtered. The organic layer of the filtrate is washed with water and saturated sodium bicarbonate solution and then dried giving a brown semi-solid. This semi-solid is taken up in chloroform and filtered through a short silica gel column giving 3-chloro-6-(p-fluorophenyl)-1,2,4-triazine as a tan solid.

A solution of 9.8 g. of 3-chloro-6-(p-fluorophenyl)-1,2,4-triazine in 125 ml. of pyridine is cooled to 0° C. and 15 ml. of hydrazine hydrate is added. The mixture is stirred at room temperature for one hour and then poured into icewater. The solid is recovered by filtration and washed with ethanol, giving 3-hydrazino-6-(p-fluorophenyl)-1,2,4-triazine as an orange solid.

A mixture of 3.09 g. of 3-hydrazino-6-(p-fluorophenyl)-1,2,4-triazine and 35 ml. of ethyl orthoformate is refluxed for 2 hours, cooled and poured into hexane. The solid is collected and washed with ethanol giving the desired product as a brown solid, m.p. 231°–235° C.

EXAMPLE 13

6-(p-Fluorophenyl)-3-methyl-1,2,4-triazolo[4,3-b]-1,2,4-triazine

A mixture of 3.09 g. of 3-hydrazino-6-(p-fluorophenyl)-1,2,4-triazine and 35 ml. of ethyl orthoacetate is refluxed for 4 hours, cooled, poured into hexane and the solid is collected, and washed with ethanol giving the desired product as a brown solid, m.p. 147°–150° C.

EXAMPLE 14

6-(o-Chlorophenyl)-1,2,4-triazolo[4,3-b]-1,2,4-triazine

To a solution of 83.25 g. of selenium dioxide in 560 ml. of dioxane and 17 ml. of water at 55° C. is added 115.5 g. of o-chloroacetophenone. As in Example 12 the product is reacted with 57.6 g. of acetone oxime, giving o-chlorophenylglyoxaldoxime.

A solution of 108 g. of o-chlorophenylglyoxaldoxime, 65.6 g. of semicarbazide hydrochloride and 80.3 g. of sodium acetate trihydrate in 600 ml. of 50% ethanol is heated to 50°–60° C. for 3 hours. The solid is collected by filtration, washed with water and recrystallized from one liter of 50% aqueous ethanol giving o-chlorophenylglyoxaldoxime semicarbazone as a white solid.

A mixture of 98 g. of o-chlorophenylglyoxaldoxime semicarbazone and 2640 ml. of 5% hydrochloric acid is reacted as described in Example 12, giving 6-(o-chlorophenyl)-1,2,4-triazin-3(2H)-one as a cream-colored solid.

A suspension of 53 g. of 6-(o-chlorophenyl)-1,2,4-triazin-3(2H)-one in 400 ml. of chloroform is cooled in an ice bath and 400 ml. of phosphorus oxychloride is added followed by 3 g. of N,N-dimethylformamide. The mixture is refluxed overnight and treated as described in Example 12, giving 3-chloro-6-(o-chlorophenyl)-1,2,4-triazine as white needles.

A solution of 19.8 g. of 3-chloro-6-(o-chlorophenyl)-1,2,4-triazine in 120 ml. of pyridine is treated with 15 g. of hydrazine hydrate as described in Example 12, giving 6-(o-chlorophenyl)-3-hydrazino-1,2,4-triazine as yellow needles.

A mixture of 4.45 g. of 6-(o-chlorophenyl)-3-hydrazino--1,2,4-triazine and 50 ml. of ethyl orthoformate is refluxed for 4 hours and then cooled, giving the desired product as yellow crystals, m.p. 145°–148° C.

EXAMPLE 15

6-(o-Fluorophenyl)-1,2,4-triazolo[4,3-b]-1,2,4-triazine

A 100 g. portion of o-fluoroacetophenone is converted to o-fluorophenylglyoxaldoxime using the method of Example 12, with 80 g. of selenium dioxide, 550 ml. of dioxane, 17 ml. of water and 55.6 g. of acetone oxime.

A 71.5 g. portion of o-fluorophenylglyoxaldoxime is reacted as described in Example 12, giving o-fluorophenylglyoxaldoxime semicarbazone as a white solid.

A 61 g. portion of o-fluorophenylglyoxaldoxime semicarbazone is reacted as described in Example 12, giving 6-(o-fluorophenyl)-1,2,4-triazin-3(2H)-one.

A suspension of 42.4 g. of 6-(o-fluorophenyl)-1,2,4-triazin-3(2H)-one in 350 ml. of chloroform is refluxed overnight, cooled in an ice bath, and 350 ml. of phosphorus oxychloride followed by 2.6 g. of N,N-dimethylformamide are added. The mixture is refluxed for 4.5 hours, cooled and concentrated to a brown oil. This oil is dissolved in methylene chloride, poured onto ice and made basic, giving a brown solid. The mixture is filtered and the filtrate is passed through a silica gel column giving a crystalline solid. This solid is heated with hexane and filtered giving crystals. Recrystallization from hexane gives a tan solid which sublimes on heating giving 3-chloro-6-(o-fluorophenyl)-1,2,4-triazine as tan crystals.

A 17.9 g. portion of 3-chloro-6-(o-fluorophenyl)-1,2,4-triazine is dissolved in 120 ml. of pyridine and cooled in an ice bath. An 8.5 g. portion of hydrazine hydrate is added and the mixture is heated at 60° C. for one hour and then cooled, poured into ice water and filtered giving 6-(o-fluorophenyl)-3-hydrazino-1,2,4-triazine as yellow plates.

A mixture of 3.8 g. of 6-(o-fluorophenyl)-3-hydrazino-1,2,4-triazine and 40 ml. of ethyl orthoformate is refluxed for 4 hours, cooled and poured into hexane. The solid is separated and washed with ethanol, giving the desired product as a yellow solid, m.p. 193°–196° C.

EXAMPLE 16

6-(o-Fluorophenyl)-3-methyl-1,2,4-triazolo[4,3-b]-1,2,4-triazine

A mixture of 3.8 g. of 6-(o-fluorophenyl)-3-hydrazino-1,2,4-triazine and 40 ml. of ethyl orthoacetate is refluxed for 4 hours, cooled and the solid is collected by filtration and washed with hexane, giving the desired product as a yellow solid, m.p. 199.5°–203.5° C.

EXAMPLE 17

6-(o-Chlorophenyl)-3-methyl-1,2,4-triazolo[4,3-b]-1,2,4-triazine

A mixture of 4.45 g. of 6-(o-chlorophenyl)-3-hydrazino-1,2,4-triazine and 50 ml. of ethyl orthoacetate is treated as described in Example 16, giving the desired product as yellow crystals, m.p. 172°–175° C.

EXAMPLE 18

6-($\alpha,\alpha,\alpha$-Trifluoro-m-tolyl)-1,2,4-triazolo[4,3-b]-1,2,4-triazine overnight A 50 g. portion of m-trifluoromethylacetophenone is converted to ($\alpha,\alpha,\alpha$-trifluoro-m-tolyl)glyoxaldoxime by the procedure described in Example 12.

A solution of 35.6 g. of ($\alpha,\alpha,\alpha$-trifluoro-m-tolyl)-glyoxaldoxime, 18.3 g. of semicarbazide hydrochloride and 22.4 g. of sodium acetate trihydrate in 200 ml. of 50% ethanol is heated to 50° C. The solid which forms is collected and recrystallized from chloroform-hexane, giving ($\alpha,\alpha,\alpha$-trifluoro-m-tolyl)glyoxaldoxime semicarbazone as colorless needles.

A 50 g. portion of ($\alpha,\alpha,\alpha$-trifluoro-m-tolyl)glyoxaldoxime semicarbazone in 1140 ml. of 5% hydrochloric acid is refluxed for one hour, cooled and the solid collected by filtration. This solid is refluxed in 200 ml. of acetic acid overnight and the solvent removed. The residue is dissolved in ether and then hexane is added giving 6-($\alpha,\alpha,\alpha$-trifluoro-m-tolyl)-1,2,4-trizin-3(2H)-one as a yellow solid.

A 37.2 g. portion of 6-($\alpha,\alpha,\alpha$-trifluoro-m-tolyl)-1,2,4-triazin-3(2H)-one in 250 ml. of chloroform is refluxed overnight and then cooled. A 250 ml. portion of phosphorus oxychloride and 1.7 g. of N,N-dimethylformamide are added and the mixture is refluxed for 4.5 hours and then concentrated to a brown oil. This oil is dissolved in methylene chloride and poured into ice-water. The mixture is filtered through silica gel giving crystals which are recrystallized from hexane, giving 3-chloro-6-($\alpha,\alpha,\alpha$-trifluoro-m-tolyl)-1,2,4-triazine as reddish plates.

A solution of 5.1 g. of 3-chloro-6-($\alpha,\alpha,\alpha$-trifluoro-m-tolyl)-1,2,4-triazine in 30 ml. of pyridine is cooled to 0° C. and 3.5 ml. of hydrazine hydrate is added. The mixture is heated to 60° C., maintained at 60° C. for one hour, cooled and poured into ice-water. The resulting slurry is filtered and the solid is washed with ethanol giving 3-hydrazino-6-($\alpha,\alpha,\alpha$-trifluoro-m-tolyl)-1,2,4-triazine as a yellow solid.

A mixture of one gram of 3-hydrazino-6-($\alpha,\alpha,\alpha$-trifluoro-m-tolyl)-1,2,4-triazine and 15 ml. of ethyl orthoformate is refluxed for 4 hours, cooled and poured into hexane. The solid is collected by filtration and washed with ethanol giving the desired product, m.p. 229°–232° C.

EXAMPLE 19

3-Methyl-6-($\alpha,\alpha,\alpha$-trifluoro-m-tolyl)-1,2,4-triazolo[4,3-b]-1,2,4-triazine A mixture of 2.65 g. of 3-hydrazino-6-($\alpha,\alpha,\alpha$-trifluoro-m-tolyl)-1,2,4-triazine and 30 ml. of ethyl orthoacetate is refluxed for 4 hours, and then cooled. The solid is recovered by filtration and washed with hexane giving the desired product as a yellow solid, m.p. 265°–268.5° C.

We claim:

1. A compound selected from the group consisting of those of the formulae:

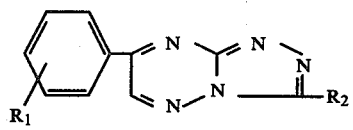

(I)

and

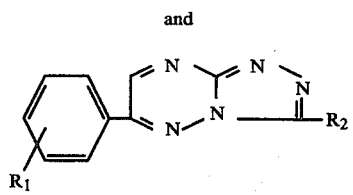

(II)

wherein $R_1$ is halogen, trifluoromethyl or lower alkoxy and $R_2$ is hydrogen or lower alkyl.

2. The compound according to claim 1, formula (I) thereof, wherein $R_1$ is para-chloro and $R_2$ is methyl; 3-methyl-7-(p-chlorophenyl)-1,2,4-triazolo[4,3-b]-1,2,4triazine.

3. The compound according to claim 1, formula (II) thereof, wherein $R_1$ is meta-methoxy and $R_2$ is hydrogen; 7-(m-methoxyphenyl)-1,2,4-triazolo[4,3-b]-1,2,4-triazine.

4. The compound according to claim 1, formula (I) therof, wherein $R_1$ is meta-trifluoromethyl and $R_2$ is methyl; 3-methyl-7-($\alpha,\alpha,\alpha$-trifluoro-m-tolyl)-1,2,4-triazolo[4,3-b]-1,2,4-triazine.

5. The compound according to claim 1, formula (II) thereof, wherein $R_1$ is meta-fluoro and $R_2$ is methyl; 3-methyl-6-(m-fluorophenyl)-1,2,4-triazolo[4,3-b]-1,2,4-triazine.

6. The compound according to claim 1, formula II thereof, wherein $R_1$ is meta-trifluoromethyl and $R_2$ is methyl; 3-methyl-6-($\alpha,\alpha,\alpha$-trifluoro-m-tolyl)-1,2,4-triazolo[4,3-b]-1,2,4-triazine.

7. The compound according to claim 1, formula II thereof, wherein $R_1$ is meta-chloro and $R_2$ is methyl; 3-methyl-6-(m-chlorophenyl)-1,2,4-triazolo[4,3-b]-1,2,4-triazine.

8. The compound according to claim 1, formula II thereof, wherein $R_1$ is meta-trifluoromethyl and $R_2$ is hydrogen; 6-(m-trifluorophenyl)-1,2,4-triazolo[4,3-b]-1,2,4-triazine.

* * * * *